(12) United States Patent
Deruelle et al.

(10) Patent No.: US 8,328,929 B2
(45) Date of Patent: Dec. 11, 2012

(54) CATIONICALLY CURABLE SILICONE COMPOSITIONS BASED ON COLLOIDAL SILICA AND ANTI-MIST/ANTI-FOULING HARD COATINGS FORMED THEREFROM

(75) Inventors: Martial Deruelle, Millery (FR);
Jean-Marc Frances, Meyzieu (FR);
Michel Feder, Villeurbanne (FR)

(73) Assignee: Bluestar Silicones France SAS, Lyons (FR)

( * ) Notice: Subject to any disclaimer, the term of this patent is extended or adjusted under 35 U.S.C. 154(b) by 0 days.

(21) Appl. No.: 11/727,402

(22) Filed: Mar. 26, 2007

(65) Prior Publication Data
US 2008/0064832 A1    Mar. 13, 2008

Related U.S. Application Data

(63) Continuation of application No. 11/153,622, filed on Jun. 16, 2005, now abandoned, and a continuation of application No. PCT/FR03/03614, filed on Dec. 8, 2003.

(30) Foreign Application Priority Data

Dec. 16, 2002  (FR) ..................................... 02 15946

(51) Int. Cl.
*C08K 3/00* (2006.01)
(52) U.S. Cl. .............. 106/287.15; 106/287.13; 524/588; 524/858; 524/868
(58) Field of Classification Search ............. 106/287.13, 106/287.15; 524/588, 858, 868
See application file for complete search history.

(56) References Cited

U.S. PATENT DOCUMENTS

| | | | | |
|---|---|---|---|---|
| 5,340,898 A | * | 8/1994 | Cavezzan et al. | 528/19 |
| 5,385,955 A | * | 1/1995 | Tarshiani et al. | 522/31 |
| 6,514,574 B1 | * | 2/2003 | Valeri et al. | 427/515 |
| 6,673,397 B2 | * | 1/2004 | Malik | 427/505 |
| 2003/0050358 A1 | * | 3/2003 | Wang | 522/83 |
| 2003/0068486 A1 | * | 4/2003 | Arney et al. | 428/323 |
| 2011/0027702 A1 | * | 2/2011 | Qiu et al. | 430/5 |

* cited by examiner

*Primary Examiner* — Margaret Moore
(74) *Attorney, Agent, or Firm* — SNR Denton US LLP

(57) ABSTRACT

Silicone compositions that are cationically crosslinkable into hard, anti-mist/anti-fouling coatings, e.g., onto thermoplastic substrates, contain colloidal particles of non-functionalized silica and also:
  at least one crosslinkable and/or polymerizable silicone monomer, oligomer and/or polymer comprising:
  at least one structural unit of formula (I):

$$Z^1(R^0)_a SiO_{(3-a)/2} \qquad (I)$$

in which:
  $a = 0$, 1 or 2;
  the radicals $R^0$, which may be identical or different when $a > 1$, are each an alkyl, cycloalkyl, aryl, vinyl, or alkoxy radical, or a hydrogen atom;
  the radicals $Z^1$, which may be identical or different when the number of units of formula (I) is greater than 1, are each an organic substituent comprising at least one epoxy and/or alkenyl ether and/or oxetane and/or dioxolane and/or carbonate reactive functional group;
  and a total number of silicon atoms per molecule at least equal to 2; and
an effective amount of at least one cationic initiator; and optionally, at least one organic solvent.

17 Claims, No Drawings

CATIONICALLY CURABLE SILICONE COMPOSITIONS BASED ON COLLOIDAL SILICA AND ANTI-MIST/ANTI-FOULING HARD COATINGS FORMED THEREFROM

CROSS-REFERENCE TO PRIORITY/PCT APPLICATIONS

This application claims priority under 35 U.S.C. §119 of FR 02/15946, filed Dec. 16, 2002, and is a continuation of U.S. application Ser. No. 11/153,622 filed Jun. 16, 2005, now abandoned, PCT/FR 2003/003614, filed Dec. 8, 2003 and designating the United States (published in the French language on Jul. 29, 2004 as WO 2004/063300 A1; the title and abstract were also published in English), each hereby expressly incorporated by reference and each assigned to the assignee hereof.

BACKGROUND OF THE INVENTION

1. Technical Field of the Invention

The present invention relates to compositions which can be crosslinked by the cationic route to provide hard scratch-resistant coatings.

More preferably, the present invention relates to compositions which can be crosslinked by the cationic route to provide hard coatings furthermore exhibiting anti-fouling and/or anti-mist properties.

2. Description of Background and/or Related and/or Prior Art

Thermoplastics, such as polycarbonate, have acquired a predominant role in numerous applications as substituents for glass. This is the case, for example, in the automobile field, where they are used for the manufacture of lenses for the headlamp units and tail lights of vehicles. This is also the case in the field of the spectacle trade, where they are used for the manufacture of spectacle glasses. The main advantage of these thermoplastics is that they are lighter and less brittle than glass.

However, these materials also exhibit a major disadvantage, namely, their low hardness in comparison with that of glass. Consequently, these materials are more easily subject to scratching and to detrimental changes, even in the context of normal use.

Need thus continues to exist for solutions to limit these problems of scratching and of detrimental change.

One of the solutions employed consists in producing a hard coating at the surface of the thermoplastic, in the form of a transparent laminate intended to improve the performance of the thermoplastic. Numerous documents of the state of the art disclose compositions intended to form this type of coating.

Compositions based on epoxyalkoxysilanes which can be crosslinked by the thermal route are described in U.S. Pat. No. 4,211,823. These compositions make it possible to obtain hard polysiloxane coatings.

A significant disadvantage of these compositions is the time necessary for the crosslinking.

WO-A-94/10230 provides an improvement for avoiding excessively long crosslinking times. This improvement consists in using ultraviolet radiation as means for activating the crosslinking. However, a disadvantage of these compositions is that of having a poorer resistance to abrasion than that of the coatings crosslinked by the thermal route.

In order to overcome this disadvantage, WO-A-02/00561 claims a process for the manufacture of a coating obtained by crosslinking, by the cationic route, an epoxy monomer essentially based on glycidyl, first by photopolymerization and then by thermal post-crosslinking in the presence of a thermal crosslinking catalyst.

U.S. Pat. No. 6,210,790 claims a colloidal silica modified by epoxy or propenyl ether groups and introduced into compositions which can be crosslinked by the cationic route to give a hard coating. The colloidal silica is grafted with the alkoxysilane in water. In addition to the silica functionalized by the alkoxysilane, the composition comprises multifunctional monomers and in particular siloxane monomers with epoxy units and a cationic initiator of onium salt type.

One disadvantage of the technique described in this patent is, first, that it involves the preliminary functionalization of the colloidal silica by an alkoxysilane and, secondly, that it is necessary to remove the solvent for functionalization of the silica before carrying out the crosslinking.

Furthermore, the industries in the technical fields under consideration remain vigilant for hard coatings also having anti-mist and/or anti-fouling properties.

Some prior documents disclose means which make it possible to obtain anti-mist or anti-fouling properties have already been described.

This is the case in particular with WO-A-02/12404, which describes a hard coating based on colloidal silicas which are functionalized by acrylates for optical devices exhibiting anti-fouling properties via a layer of perfluoropolyether deposited on the hard coating.

FR-A-2,749,587 describes a composition which can be crosslinked by radiation to give a hard coating exhibiting anti-mist properties. This composition comprises a colloidal silica, an olefin comprising at least two sites of unsaturation and at least one divalent oxyalkylene radical, and a trialkoxysilane comprising an olefinic functional group.

The anti-mist coating obtained from the composition described in FR-A-2,749,587 has the principal disadvantage of being sensitive to inhibition by atmospheric oxygen.

However, no composition of the prior art is capable of providing a hard coating jointly exhibiting anti-mist and anti-fouling properties. This is because the mechanisms of the anti-mist and anti-fouling properties are generally incompatible.

SUMMARY OF THE INVENTION

Novel compositions which can be cured by the cationic route to provide hard coatings have now been discovered.

Briefly, the present invention features compositions capable of forming hard coatings exhibiting anti-mist and/or anti-fouling properties.

The present invention also features compositions capable of forming coatings possessing permanent anti-mist and/or anti-fouling properties.

Thus, the present invention features compositions which can be crosslinked by the cationic route to provide hard coating, comprising colloidal particles of non-functionalized silica, and additionally which comprise:

at least one crosslinkable and/or polymerizable silicone monomer, oligomer and/or polymer comprising:

at least one structural unit of formula (I):

$$Z^1(R^0)_a SiO_{(3-a)/2} \quad (I)$$

in which:

a=0, 1 or 2;

the radicals $R^0$, which may be identical or different when a>1, are each an alkyl, cycloalkyl, aryl, vinyl, or alkoxy radical, or a hydrogen atom, preferably a lower $C_1$-$C_6$ alkyl radical;

the radicals $Z^1$, which may be identical or different when the number of units of formula (I) is greater than 1, are each an organic substituent comprising at least one epoxy and/or alkenyl ether and/or oxetane and/or dioxolane and/or carbonate reactive functional group, $Z^1$ preferably being an organic substituent comprising at least one epoxy and/or dioxolane reactive functional group;

and a total number of silicon atoms per molecule at least equal to 2, and an effective amount of at least one cationic initiator, and optionally, at least one organic solvent.

DETAILED DESCRIPTION OF BEST MODE AND SPECIFIC/PREFERRED EMBODIMENTS OF THE INVENTION

The term "hard coating" means a coating having a pencil hardness at least equal to H.

Advantageously, the subject compositions additionally comprise, as anti-mist compound, at least one crosslinkable and/or polymerizable silicone monomer, oligomer and/or polymer comprising at least one structural unit of formula (II):

$$Z^2(R^0)_a SiO_{(3-a)/2} \quad (II)$$

in which:

a=0, 1 or 2;

$R^0$ is as defined above;

the radicals $Z^2$, which may be identical or different when the number of units of formula (II) is greater than 1, are each an organic substituent comprising at least one oxyalkyl or polyoxyalkyl functional group $((CH_2)_m O)_x$ or $(CH_2-CH(CH_3)-O)_y$, or copolymers, said monomer, oligomer and/or polymer exhibiting a viscosity of less than 500 mPa·s and preferably less than 300 mPa·s.

An effective compound can be, by way of example, a mixture of a silicone-polyether block copolymer and of free polyether sold under the reference Rhodorsil® Oil 10646.

An effective organic compound can also be a vinyl ether sold under the reference Rapicure® DPE2 (CAS No. 765-12-8), DVE3 (CAS No. 114188-95-3) or DPE3 (114266-85-2).

This is because it participates in the cationic polymerization and is incorporated in the network, rendering the treatment very effective.

Other anti-mist compounds can, for example, be sodium sulfosuccinate.

The anti-mist compound can also be any surfactant comprising hydrophilic groups, such as polyoxyethylene, polyoxypropylene, alkali metal sulfate, sulfonate or carboxylate, polyols, amine salts or quaternary amines.

More advantageously still, the compositions according to the invention comprise, as anti-fouling compound, at least one crosslinkable and/or polymerizable silicone monomer, oligomer and/or polymer comprising at least one structural unit of formula (III):

$$Z^3(R^0)_a SiO_{(3-a)/2} \quad (III)$$

in which:

a=0, 1 or 2, the radicals $R^0$, which may be identical or different, are each an alkyl, cycloalkyl, aryl, vinyl, or alkoxy radical, or a hydrogen atom, preferably a lower $C_1$-$C_6$ alkyl radical;

the radicals $Z^3$, which may be identical or different when the number of units of formula (III) is greater than 1, are each an organic substituent comprising at least one $(C_nF_{2n+1})$—$(R^0)_a$ group with n<20; and/or one perfluoropolyether compound of formula (IV):

$$Y-(C_aF_{2a}O)_b-C_aF_{2a}-Y \quad (IV)$$

in which:

Y is a polymerizable group or a fluorine or hydrogen atom;

a ranges from 1 to 7;

b ranges from 1 to 300, such that said perfluoropolyether compound has an average molecular mass of from 500 to 20,000.

The most effective organic compounds are:

perfluorinated compounds including an epoxide or vinyl ether functional group, such as glycidyl octafluoropentyl ether, glycidyl tetrafluoroethyl ether, glycidyl tetrafluoropropyl ether, glycidyl hexadecafluorononyl ether, glycidyl dodecafluoroheptyl ether, heptadecafluorononyloxirane, heptafluorobutyloxirane, hexadecafluorononyl ether, hexadecafluoro-8-(trifluoromethyl)nonyloxirane, dodecafluoro-6-(trifluoromethyl)heptyloxirane, octafluoropentanol, heptadecafluorononanol, heptadecafluorodecanol, and the like, Asahi Glass products, such as the $C_8F_{17}$ oxirane.

Thus, the perfluoropolyether compound can be selected from the group consisting of:

$(C_2H_5O)_2CH_3SiC_3H_6NHCO(CF_2O)_{15}(C_2F_4O)_{13}CF_2CONHC_3H_6SiCH_3(OC_2H_5)_2$, $(C_2H_5O)_3SiC_3H_6NHCO(CF_2O)_{15}(C_2F_4O)_{13}CF_2CONHC_3H_6Si(OC_2H_5)_3$, $F(CF(CF_3)CF_2O)_{25}CF_2CF_3$, $C_4H_9NHCO(CF_2O)_{15}(C_2F_4O)_{13}CF_2CONHC_4H_9$, $CH_2=CHCOOC_2H_4NHCO(CF_2O)_{15}(C_2F_4O)_{13}CF_2CONHC_2H_4OOCCH=CH_2$, $CH_2=CHCOOCH_2(CF_2O)_{15}(C_2F_4O)_{13}CF_2CH_2OOCCH=CH_2$, $(HOCH_2)_2CH_2NHCO(CF_2O)_{15}(C_2F_4O)_{13}CF_2CONHCH_2(CH_2OH)_2$, $(C_2H_5O)_3Si(CH_2)_3NHCO(CF_2CF_2O)_8CF_2CONH(CH_2)_3Si(OC_2H_5)_3$, $(C_2H_5O)_2CH_3Si(CH_2)_3NHCO(CF_2CF_2O)_8CF_2CONH(CH_2)_3SiCH_3(OC_2H_5)_2$, $(C_2H_5O)_2CH_3Si(CH_2)_3NHCO(CF_2CF_2O)_{14}CF_2CONH(CH_2)_3SiCH_3(OC_2H_5)_2$, $(C_2H_5O)_3Si(CH_2)_3NHCO(CF_2C(CF_3)FO)_{12}CF_2CONH(CH_2)_3Si(OC_2H_5)_3$, $(C_2H_5O)_2CH_3Si(CH_2)_3NHCO(CF_2C(CF_3)FO)_{12}CF_2CONH(CH_2)_3SiCH_3(OC_2H_5)_2$ or $OOCCH=CH_2OOCCH=CH_2$ $H_2C=HCCOO-CH_2CHCH_2NHCO(CF_2O)_{15}(CF_2CF_2O)_{13}CF_2CONHCH_2CHCH_2-OOCCH=CH_2$

According to a first embodiment, the cationic initiator can be selected from among those having a cationic moiety selected from onium ions of formula (V):

$$[(R^1)_n-A-(R^2)_m]^+ \quad (V)$$

in which:

A represents an element from Groups 15 to 17 of the Periodic Table, such as, for example: I, S, Se, P or N.

$R^1$ represents a $C_6$-$C_{20}$ carbocyclic or heterocyclic aryl radical, it being possible for said heterocyclic radical to comprise nitrogen or sulfur as heteroelements, $R^2$ represents $R^1$ or a linear or branched $C_1$-$C_{30}$ alkyl or alkenyl radical, said $R^1$ and $R^2$ radicals optionally being substituted by a $C_1$-$C_{25}$ alkoxy, $C_1$-$C_{25}$ alkyl, nitro, chloro, bromo, cyano, carboxyl, ester or mercapto group, n is an integer ranging from 1 to v+1, v being the valency of the element A, m is an integer ranging from 0 to v−1, with n+m=v+1.

Preferably, the anionic moiety of the initiator is a borate of formula (VI):

$$[BX_aR_b]^-  \quad (VI)$$

in which:

a and b are integers ranging, for a, from 0 to 3 and, for b, from 1 to 4, with a+b=4, the X symbols represent:

a halogen atom (chlorine, fluorine) with a=0 to 3, an OH functional group with a=0 to 2, the R symbols are identical or different and represent:

a phenyl radical substituted by at least one electron-withdrawing group, such as, for example, $OCF_3$, $CF_3$, $NO_2$ or CN, and/or by at least 2 halogen atoms (very particularly fluorine), this being the case when the cationic entity is an onium of an element from Groups 15 to 17, a phenyl radical substituted by at least one electron-withdrawing element or group, in particular a halogen atom (very particularly fluorine), $CF_3$, $OCF_3$, $NO_2$ or CN, this being the case when the cationic entity is an organometallic complex of an element from Groups 4 to 10, an aryl radical comprising at least two aromatic rings, such as, for example, biphenyl or naphthyl, optionally substituted by at least one electron-withdrawing element or group, in particular a halogen atom, including in particular fluorine, $OCF_3$, $CF_3$, $NO_2$ or CN, whatever the cationic entity.

The initiator can advantageously be selected from the group consisting of:

$[(C_8H_{17})-O-\Phi-I-\Phi]^+[B(C_6F_5)_4]^-$, $[(CH_3)_2-CH-\Phi-I-\Phi-CH_3]^+[B(C_6F_5)_4]^-$ $[C_{12}H_{25}-\Phi-I-\Phi]^+[B(C_6F_5)_4]^-$, $[(C_8H_{17}-O-\Phi)_2I]^+[B(C_6F_5)_4]^-$ $[(C_8H_{17})-O-\Phi-I-\Phi]^+[B(C_6F_5)_4]^-$, $[(\Phi)_3S]^+[B(C_6F_5)_4]^-$ $[(\Phi)_2S-\Phi-O-C_8H_{17}]^+[B(C_6H_4CF_3)_4]^-$, $[(C_{12}H_{25}-\Phi)_2I]^+[B(C_6F_5)_4]^-$ $[(CH_3)_2-CH-\Phi-I-\Phi-CH_3]^+[B(C_6H_3(CF_3)_2)_4]^-$ $(\eta^5\text{-cyclopentadienyl})(\eta^6\text{-toluene})Fe^+[B(C_6F_5)_4]^-$ $(\eta^5\text{-cyclopentadienyl})(\eta^6\text{-1-methylnaphthalene})Fe^+[B(C_6F_5)_4]^-$ $(\eta^5\text{-cyclopentadienyl})(\eta^6\text{-cumene})Fe^+[B(C_6F_5)_4]^-$ According to an alternative embodiment of the invention, the initiator can also be a nontoxic onium salt having a cationic structure of formula (VII):

$$[(CH(CH_3)_2-\Phi-I-(-R^1)]^+ \quad (VII)$$

in which the symbol $R^1$ represents the -$\Phi$-$R^2$ radical, $R^2$ being a linear or branched alkyl radical comprising from 1 to 20 carbon atoms, preferably 1 to 15 carbon atoms.

The anionic structure of the onium salt is selected from the group consisting of: $Cl^-$, $Br^-$, $BF_4^-$, $PF_6^-$, $CF_3SO_3^-$, $N(SO_2CF_3)_2^-$, $CH(SO_2CF_3)_2^-$, $B(C_6F_5)_4^-$, $B(PhOCF_3)_4^-$, $SbF_6^-$ and/or $AsF_6^-$. However, the following initiators have proved to be particularly advantageous:

$[(CH(CH_3)_2-\Phi-)-I-\Phi-CH_3]^+B(C_6F_5)_4^-$ $[(CH(CH_3)_2-\Phi-)-I-\Phi-CH_3]^+PF_6^-[(CH(CH_3)_2-\Phi-)-I-\Phi-CH_3]^+B(PhOCF_3)_4^-$ $[(CH_3)_2-CH-\Phi-I-\Phi-CH_3]^+[B(C_6H_3(CF_3)_2)_4]]^-$

Such initiators are describe in the document FR-A-2 762 001.

The silicone oligomer is represented by the following formula (VIII):

$$Z^4Si(R^0)_aO_{(3-a)/2}$$

in which:

a=0, 1 or 2, the radicals $R^0$, which may be identical or different, are each an alkyl, cycloalkyl, aryl, vinyl, or alkoxy radical, or a hydrogen atom, preferably a lower $C_1$-$C_6$ alkyl radical, $Z^4$ is selected in particular from among the following radicals:

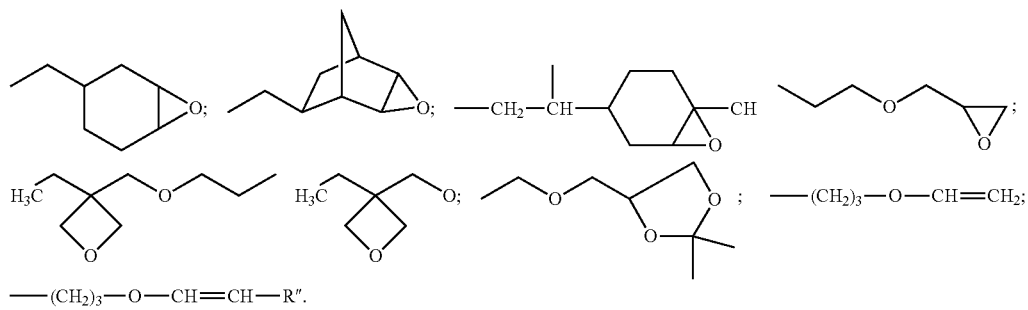

The silicone oligomer of formula (VIII) can comprise the following structures:

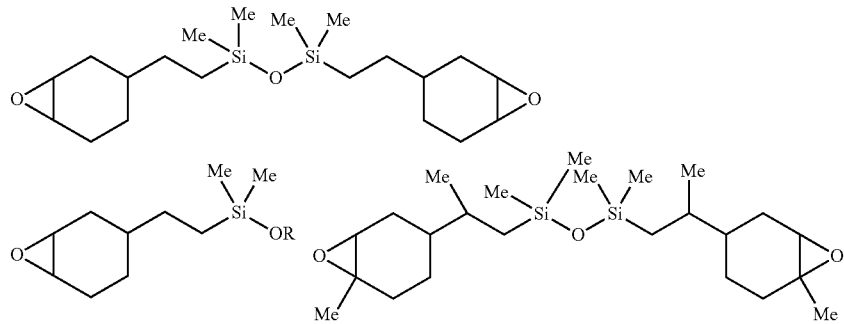

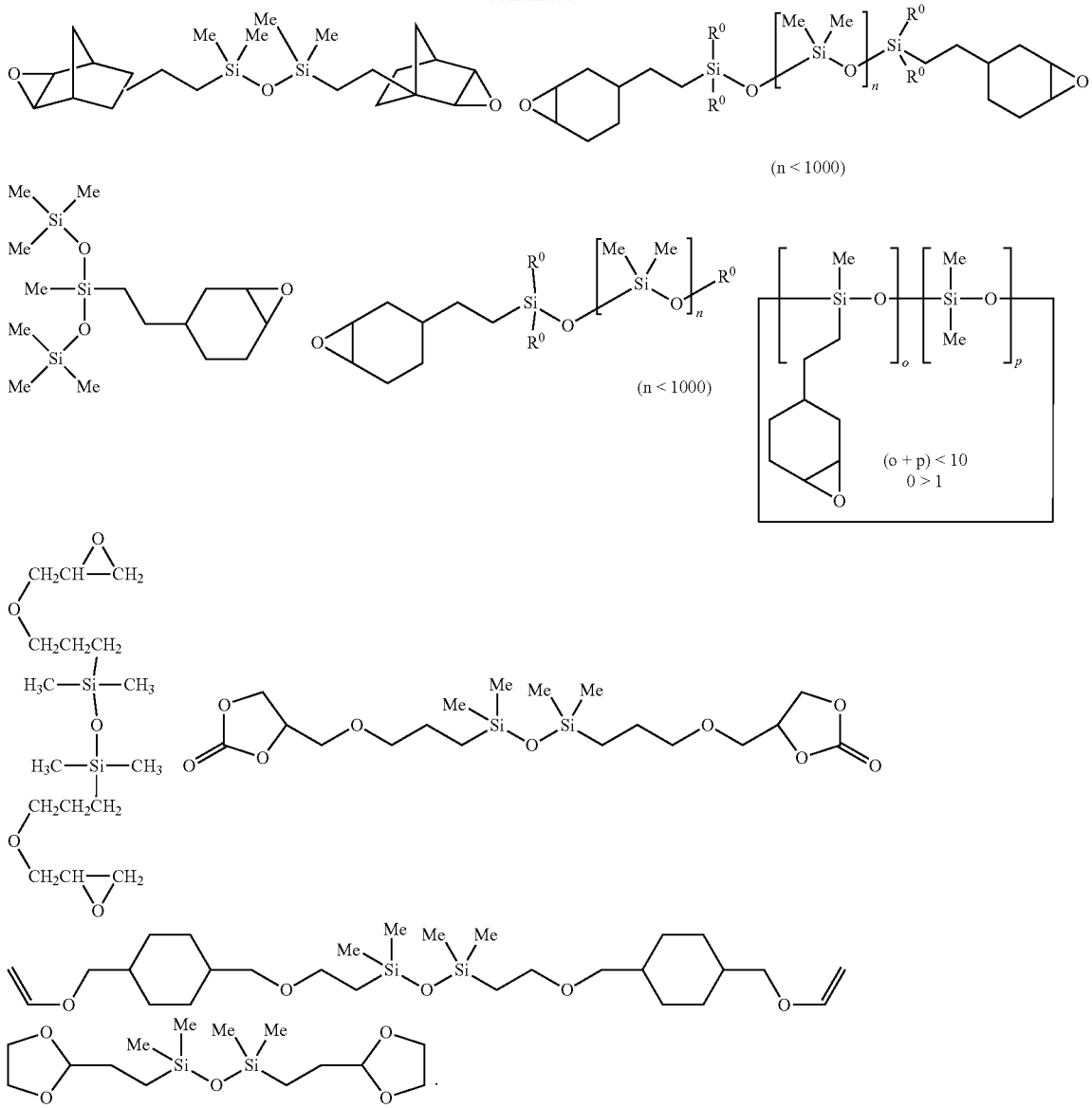

The silica used can be of various origins: precipitated silica, fumed silica, silica aerogels, silica sol and/or natural silica.

According to a preferred embodiment of the invention, the amorphous silica present predominantly or entirely in the silicone phase results from silica sol and more particularly from silica organosols; a general description of silica sols is given in U.S. Pat. No. 2,801,185 and in "The Colloid Chemistry of Silica and Silicates" (Ralph K. Iler, Cornell University Press, 1955; see in particular pages 120-121).

Mention may be made, as examples of commercial silica organosols, of those from Clariant, Fuso Chemicals, Nalco, Degussa-Huls and DuPont Chemicals.

Mention will be made, for Clariant, of the following products: Highlink® OG1-32, Highlink® OG8-32, Highlink® OG401-31, Highlink® OG502-30, Highlink® OG502-31 and Highlink® OG600-51.

The silica particles exhibit a mean diameter of less than 1 μm and more preferably of from 50 to 500 nm.

It should be noted that the colloidal or fumed silica used to reinforce the coating is conveyed in an organic solvent and in particular an alcoholic solvent, such as primary, secondary or tertiary alcohols. Isopropanol or diacetone alcohol are solvents of choice.

Use may also be made of ketones, tetrahydrofuran, hydrocarbon fractions or fluorinated solvents.

Preferably, the proportion of organic solvent in the compositions according to the invention is at least equal to 10 parts by weight.

This invention also features a process for preparing a composition which can be crosslinked by the cationic route to provide a hard coating as described above, which essentially comprises the stage entailing mixing particles of non-functionalized colloidal silica with:

at least one crosslinkable and/or polymerizable silicone monomer, oligomer and/or polymer comprising at least one unit of formula (I) and a total number of silicon atoms per molecule at least equal to 2, an effective amount of at least one cationic initiator, optionally, at least one organic solvent, optionally, at least one crosslinkable and/or polymerizable silicone monomer, oligomer and/or polymer comprising at least one unit of formula (II), optionally, at least one crosslinkable and/or polymerizable silicone monomer, oligomer and/or polymer comprising at least one unit of formula (III) or one perfluoropolyether compound of formula (IV).

The present invention also features a process for preparing a hard coating on a support based on at least one thermoplastic, comprising the stages:

a) mixing a non-functionalized colloidal silica with:
   at least one crosslinkable and/or polymerizable silicone monomer, oligomer and/or polymer comprising at least one unit of formula (I) and a total number of silicon atoms per molecule at least equal to 2,
   an effective amount of at least one cationic initiator,
   optionally, at least one organic solvent,
   optionally, at least one crosslinkable and/or polymerizable silicone monomer, oligomer and/or polymer comprising at least one unit of formula (II),
   optionally, at least one crosslinkable and/or polymerizable silicone monomer, oligomer and/or polymer comprising at least one unit of formula (III) or one perfluoropolyether compound of formula (IV), b) applying the mixture obtained to the support based on at least one thermoplastic, and c) curing the composition by crosslinking by the thermal or actinic route to provide a hard coating.

Use may advantageously be made, so as to obtain a thin layer of hard coating of less than 5 microns, of a volatile organic solvent which is evaporated before irradiation. The solvent is volatilized before irradiation but can also react with the base, in the case of the alcohols which react with the oxirane functional groups during the process. In this case, a reactive diluent is present.

Finally, the present invention features hard coatings obtained from the subject compositions or by the process according to the invention.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

The products used in the compositions of the examples are as follows:

the silicone oligomer comprising an epoxide functionality of formula (A) having approximately 5% of (A')

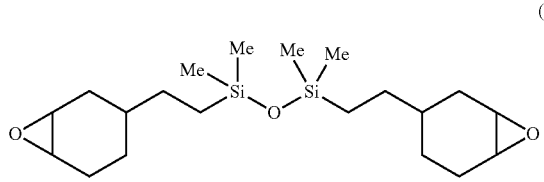

(A)

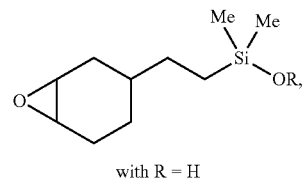

(A')

with R = H the onium borate initiator (P1):

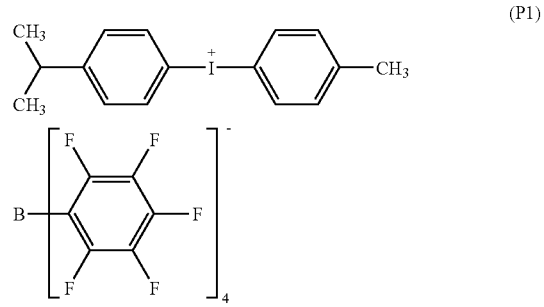

(P1)

the colloidal silicas:

Highlink OG (OG1-32 (ethylene glycol), OG8-32 (pentanediol), OG401-31 (ethylene glycol monopropyl ether), OG502-30 (isopropanol), OG502-31 (isopropanol) or OG600-51 (butyl acetate)), sold by Clariant(, Nanopox from Hanse Chemie, such as Nanopox XP 22/0314, which are reinforced with a cycloaliphatic epoxy resin.

Fumed silicas treated with acrylates, such as Aerosil R711 or Aerosil R7200 from Degussa.

Example 1

Preparation of a Flexform 40 Thermal Control Formulation

This solution is sold by Exxene for abrasion-resistant coatings.

This solution is applied by dipping to a polycarbonate sheet at 20° C. and is then dried at 25° C. for 10 min, followed by thermal crosslinking at 122° C. for 35 min.

The thickness of the film is two micrometers. A Taber abrasion resistance test is carried out according to standard T30-015 with a load of 500 g and 300 cycles with CS10-F abrasive wheels. A variation in gloss of 10% is found. % Haze=10%.

The pencil hardness of the coating ranges from 4H to 6H.

Example 2

Preparation of a UV Formulation According to the Invention without Anti-Mist Agent 10 g of siloxane resin having a content of monomer (A) of greater than 90%, obtained by hydrosilylation of 4-vinylcyclohex-1-ene epoxide (VCMX), 1.25 g of photoinitiator systems including 20% of photoinitiator P1 dissolved in isopropanol, and 40 g of Highlink colloidal silica as a 30% solution in isopropanol are charged to a beaker.

The system is stable at ambient temperature for at least 6 months with the exclusion of light and heat. The solution is applied by dipping to a polycarbonate sheet.

The sheet is allowed to drain for one minute.

The system is crosslinked by passing, at the rate of 5 m/min, over a UV bench equipped with two 160 W/cm Hg lamps. The system is dry and very hard at the outlet of the bench.

The thickness of the film is 3 micrometers.

The pencil hardness is 3H immediately and greater than 4H after 24 hours.

An annealing at 150° C. for 1 hour or under an infrared lamp for a few minutes makes it possible to obtain a hardness of 5H.

The same Taber abrasion test is used and a variation in gloss, % Haze=15%, is found.

Example 3

Preparation of a UV Formulation According to the Invention with Anti-Mist Agent 10 g of siloxane resin having a content of monomer (A) of greater than 90%, 1.25 g of photoinitiator system including 20% of photoinitiator P1 dissolved in isopropanol, 40 g of Highlink colloidal silica in solution in isopropanol, and 0.5 g of silicone polyether Rhodorsil Oil 10646 are charged to a beaker.

The system is stable at ambient temperature for at least 6 months with the exclusion of light and heat. The solution is applied by dipping to a polycarbonate sheet.

The sheet is allowed to drain for one minute.

The system is crosslinked by passing, at the rate of 5 m/min, over a UV bench equipped with two 160 W/cm Hg lamps. The system is dry and very hard at the outlet of the bench.

The thickness of the film is 3 micrometers.

The pencil hardness is 3H immediately and greater than 4H after 24 hours.

The same Taber abrasion test is used. A variation in gloss of 10% is found.

The polycarbonate glass, placed in a refrigerator at 5° C., does not fill up with mist when it is removed from the refrigerator and placed in an atmosphere at 100% relative humidity and 25° C.

Example 4

Preparation of a UV Formulation According to the Invention with Anti-Fouling Agent 10 g of siloxane resin having a content of monomer (A) of greater than 90%, 1.25 g of photoinitiator system including 20% of photoinitiator P1 dissolved in isopropanol, 38 g of Highlink colloidal silica in solution in isopropanol, and 2 g of polyfluorosilane, tridecafluoro-1,1,2,2-tetrahydrooctyltrimethoxysilane, are charged to a beaker.

The system is stable at ambient temperature for at least 6 months with the exclusion of light and heat. The solution is applied by dipping to a polycarbonate sheet.

The sheet is allowed to drain for one minute.

The system is crosslinked by passing, at the rate of 5 m/min, over a UV bench equipped with two 160 W/cm Hg lamps. The system is dry and very hard at the outlet of the bench.

The thickness of the film is 3 micrometers.

The pencil hardness is 3H immediately and greater than 4H after 24 hours.

However, a thermal post-crosslinking is carried out at 100° C. for 1 hour in order to be certain of removing traces of unreacted alkoxysilane.

The same Taber abrasion test is used. A variation in gloss of 10% is found.

Conventional inks do not leave a mark on the surface of the coating, in contrast to the thermal control based on colloidal silica and alkoxysilanes.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition crosslinkable by the cationic route to obtain a hard coating, said composition comprising:
   (a) colloidal particles of nonfunctionalized silica:
   (b) at least one crosslinkable and/or polymerizable silicone monomer, oligomer and/or polymer comprising:
   at least one structural unit of formula (I):)

$$Z^1(R^0)_a SiO_{(3-a)/2} \tag{I}$$

in which:
   a=0, 1 or 2;
   the radicals $R^0$, which may be identical or different when a>1, are each an alkyl, cycloalkyl, aryl, or vinyl radical or a hydrogen atom;
   the radicals $Z^1$, which may be identical or different when the number of units of formula (I) is greater than 1, are each an organic substituent comprising at least one epoxy and/or alkenyl ether and/or oxetane and/or dioxolane and/or carbonate reactive functional group;
   and a total number of silicon atoms per molecule at least equal to 2; and
   (c) an effective amount of at least one cationic initiator;
   (d) an antifouling compound comprising at least one perfluoropolyether compound of formula (IV):

$$Y-(C_a F_{2a}O)_b-C_a F_{2a}-Y \tag{IV}$$

in which:
   Y is a polymerizable group or a fluorine or a hydrogen;
   a ranges from 1 to 7;
   b ranges from 1 to 300,
   such that said perfluoropolyether compound has an average molecular mass of from 500 to 20,000, and
   (e) optionally, at least one organic solvent.

2. The composition as defined by claim 1, wherein said at least one cationic initiator is an onium ion of formula (V):

$$[(R^1)_n\text{-}A\text{-}(R^2)_m]^+ \tag{V}$$

in which:
   A is an element from Groups 15 to 17 of the Periodic Table;
   $R^1$ is a $C_6$-$C_{20}$ carbocyclic or heterocyclic aryl radical, said heterocyclic radical optionally comprising nitrogen or sulfur as heteroelements'
   $R^2$ is $R^1$ or a linear or branched $C_1$-$C_{30}$ alkyl or alkenyl radical, said $R^1$ and $R^2$ radicals optionally being substituted by a $C_1$-$C_{25}$ alkoxy, $C_1$-$C_{25}$ alkyl, nitro, chloro, bromo, cyano, carboxyl, ester or mercapto group;

n is an integer ranging from 1 to v+1, v being the valency of the element A; and m is an integer ranging from 0 to v−1, with n+m=v+1.

3. The composition as defined by claim 2, the anionic moiety of the initiator comprising a borate of formula (VI):

$$[BX_aR_b]^- \quad (VI)$$

in which:

a and b are integers ranging, for a, from 0 to 3 and, for b, from 1 to 4, with a+b=4;

the X symbols are each:

a halogen atom, with a=0 to 3, an OH functional group with a=0 to 2;

the R symbols, which are identical or different, are each:

a phenyl radical substituted by at least one electron-withdrawing group, and/or by at least 2 halogen atoms when the cationic moiety is an onium of an element from Groups 15 to 17 of the Periodic Table, a phenyl radical substituted by at least one electron-withdrawing element or group, when the cationic moiety is an organometallic complex of an element from Groups 4 to 10 of the Periodic Table, or an aryl radical comprising at least two aromatic rings, optionally substituted by at least one electron-withdrawing element or group whatever the cationic moiety.

4. The composition as defined by claim 1, said at least one initiator being selected from the group consisting of:

$[(C_8H_{17})\!-\!O\!-\!\Phi\!-\!I\!-\!\Phi]^+[B(C_6F_5)_4]^-$, $[(CH_3)_2\!-\!CH\!-\!\Phi\!-\!I\!-\!\Phi\!-\!CH_3]^+[B(C_6F_5)_4]^-$ $[C_{12}H_{25}\!-\!\Phi\!-\!I\!-\!\Phi]^+[B(C_6F_5)_4]^-$, $[(C_8H_{17}\!-\!O\!-\!\Phi)_2I]^+[B(C_6F_5)_4]^-$ $[(C_8H_{17})\!-\!O\!-\!\Phi\!-\!I\!-\!\Phi]^+[B(C_6F_5)_4]^-$, $[(\Phi)_3S]^+[B(C_6F_5)_4]^-$ $[(\Phi)_2S\!-\!\Phi\!-\!O\!-\!C_8H_{17}]^+[B(C_6H_4CF_3)_4]^-$, $[(C_{12}H_{25}\!-\!\Phi)_2I]^+[B(C_6F_5)_4]^-$ $[(CH_3)_2\!-\!CH\!-\!\Phi\!-\!I\!-\!\Phi\!-\!CH_3]^+[B(C_6H_3(CF_3)_2)_4]^-$ $(\eta^5\text{-cyclopentadienyl})(\eta^6\text{-toluene})Fe^+[B(C_6F_5)_4]^-$ $(\eta^5\text{-cyclopentadienyl})(\eta^6\text{-1-methylnaphthalene})Fe^+[B(C_6F_5)_4]^-$ $(\eta^5\text{-cyclopentadienyl})(\eta^6\text{-cumene})Fe^+[B(C_6F_5)_4]^-$.

5. The composition as defined by claim 1, said at least one cationic initiator comprising a nontoxic onium salt having a cationic structure of formula (VII):

$$[(CH(CH_3)_2\text{-}\Phi\text{-})\text{-I-}(\text{---}R^1)]^+ \quad (VII)$$

in which $R^1$ is the -$\Phi$-$R^2$ radical, $R^2$ being a linear or branched alkyl radical having from 1 to 20 carbon atoms.

6. The composition as defined by claim 5, the anionic structure of the onium salt being selected from the group consisting of: $Cl^-$, $Br^-$, $BF_4^-$, $PF_6^-$, $CF_3SO_3^-$, $N(SO_2CF_3)_2^-$, $CH(SO_2CF_3)_2^-$, $B(C_6F_6)_4^-$, $B(PhOCF_3)_4^-$, $SbF_6^-$ and/or $AsF_6^-$.

7. The composition as defined by claim 1, wherein the silicone oligomer has the following formula (VIII):

$$Z^4Si(R^0)_aO_{(3-a)/2} \quad (VIII)$$

in which:

a=0, 1 or 2;

the radicals $R^0$, which may be identical or different, are each an alkyl, cycloalkyl, aryl, vinyl, or alkoxy radical, or a hydrogen atom;

$Z^4$ is a radical selected from the group consisting of:

-continued

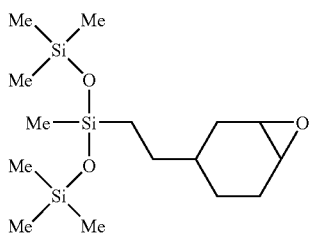 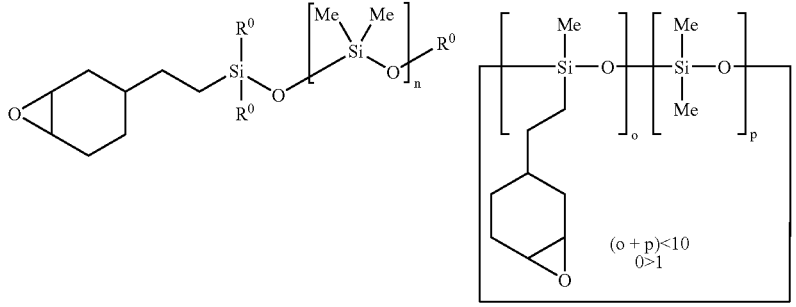

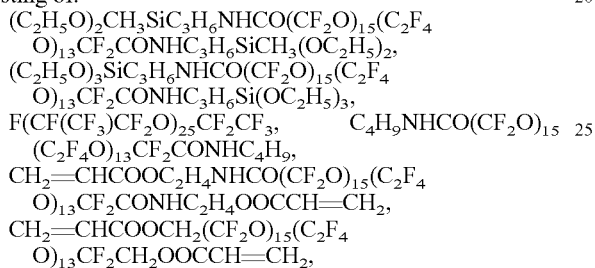

8. The composition as defined by claim 1, wherein the perfluoropolyether compound is selected from the group consisting of:

$(C_2H_5O)_2CH_3SiC_3H_6NHCO(CF_2O)_{15}(C_2F_4O)_{13}CF_2CONHC_3H_6SiCH_3(OC_2H_5)_2$, $(C_2H_5O)_3SiC_3H_6NHCO(CF_2O)_{15}(C_2F_4O)_{13}CF_2CONHC_3H_6Si(OC_2H_5)_3$, $F(CF(CF_3)CF_2O)_{25}CF_2CF_3$, $C_4H_9NHCO(CF_2O)_{15}(C_2F_4O)_{13}CF_2CONHC_4H_9$, $CH_2=CHCOOC_2H_4NHCO(CF_2O)_{15}(C_2F_4O)_{13}CF_2CONHC_2H_4OOCCH=CH_2$, $CH_2=CHCOOCH_2(CF_2O)_{15}(C_2F_4O)_{13}CF_2CH_2OOCCH=CH_2$, $(HOCH_2)_2CH_2NHCO(CF_2O)_{15}(C_2F_4O)_{13}CF_2CONHCH_2(CH_2OH)_2$, $(C_2H_5O)_3Si(CH_2)_3NHCO(CF_2CF_2O)_8CF_2CONH(CH_2)_3Si(OC_2H_5)_3$, $(C_2H_5O)_2CH_3Si(CH_2)_3NHCO(CF_2CF_2O)_8CF_2CONH(CH_2)_3SiCH_3(OC_2H_5)_2$, $(C_2H_5O)_2CH_3Si(CH_2)_3NHCO(CF_2CF_2O)_{14}CF_2CONH(CH_2)_3SiCH_3(OC_2H_5)_2$, $(C_2H_5O)_3Si(CH_2)_3NHCO(CF_2C(CF_3)FO)_{12}CF_2CONH(CH_2)_3Si(OC_2H_5)_3$, $(C_2H_5O)_2CH_3Si(CH_2)_3NHCO(CF_2C(CF_3)FO)_{12}CF_2CONH(CH_2)_3SiCH_3(OC_2H_5)_2$ and

9. The composition as defined by claim 1, said silica particles having a mean diameter of less than 1 μm.

10. The composition as defined by claim 1, comprising an alcoholic solvent.

11. The composition as defined by claim 10, the proportion of organic solvent being at least equal to 10 parts by weight.

12. The composition as defined by claim 1, in crosslinked state.

13. A substrate having a hard, anti-mist/anti-fouling coating of the composition as defined by claim 12.

14. A thermoplastic substrate having a hard, anti-mist/anti-fouling coating of the composition as defined by claim 12.

15. The composition of claim 1, wherein $R^0$ in formula (I) is a $C_1$-$C_6$ alkyl radical.

16. The composition of claim 1, wherein $Z^1$ in formula (I) is an organic substituent comprising at least one epoxy and/or dioxolane reactive functional group.

17. The composition of claim 1, wherein $R^0$ in formula (III) is a $C_1$-$C_6$ alkyl radical.

\* \* \* \* \*